United States Patent [19]
Moore

[11] Patent Number: 6,162,179
[45] Date of Patent: Dec. 19, 2000

[54] LOOP IMAGING CATHETER

[75] Inventor: Thomas C. Moore, Fremont, Calif.

[73] Assignee: Scimed Life Systems, Inc., Maple Grove, Minn.

[21] Appl. No.: 09/207,486

[22] Filed: Dec. 8, 1998

[51] Int. Cl.$^7$ .................................................. A61B 08/00
[52] U.S. Cl. ............................................................ 600/466
[58] Field of Search ...................................... 600/463, 459, 600/458, 443, 461

[56] References Cited

U.S. PATENT DOCUMENTS

| | | | |
|---|---|---|---|
| 5,215,092 | 6/1993 | Wray | 128/660.09 |
| 5,438,997 | 8/1995 | Sieben et al. | 600/463 |
| 5,570,693 | 11/1996 | Jang et al. | 600/463 |
| 5,680,683 | 10/1997 | Hossack et al. | 128/662.03 |
| 5,842,993 | 12/1998 | Eichelberger et al. | 600/462 |

FOREIGN PATENT DOCUMENTS

| | | |
|---|---|---|
| 0 061 331 A1 | 9/1982 | European Pat. Off. . |
| 0 754 429 A2 | 1/1997 | European Pat. Off. . |
| 0 774 232 A1 | 5/1997 | European Pat. Off. . |
| WO 95/06436 | 3/1995 | WIPO . |

*Primary Examiner*—Marvin M. Lateef
*Assistant Examiner*—Maulin Patel
*Attorney, Agent, or Firm*—Lyon & Lyon LLP

[57] ABSTRACT

An ultrasonic imaging catheter is used to generate a three-dimensional image of an organ having a relatively large cavity, such as, e.g., a heart. The catheter includes an elongate catheter body having an acoustic window formed at its distal end. The catheter further includes an imaging core, which includes a drive cable with a distally mounted ultrasonic transducer. The transducer is disposed in the acoustic window and is rotationally and longitudinally translatable relative thereto, providing the catheter with longitudinal scanning capability. The catheter further includes a pull wire, which is connected to the distal end of the catheter body, such that longitudinal displacement of the pull wire causes the acoustic window to bend into a known and repeatable arc. The catheter can then be operated to generate a longitudinal scan of the organ through the arc, i.e., a multitude of cross-sectional imaging data slices are generated along a continuously varying multitude of imaging planes, which intersect all regions of the body organ. In this manner, a three-dimensional image depicting the entire body organ can be generated from a single longitudinal scan.

21 Claims, 7 Drawing Sheets

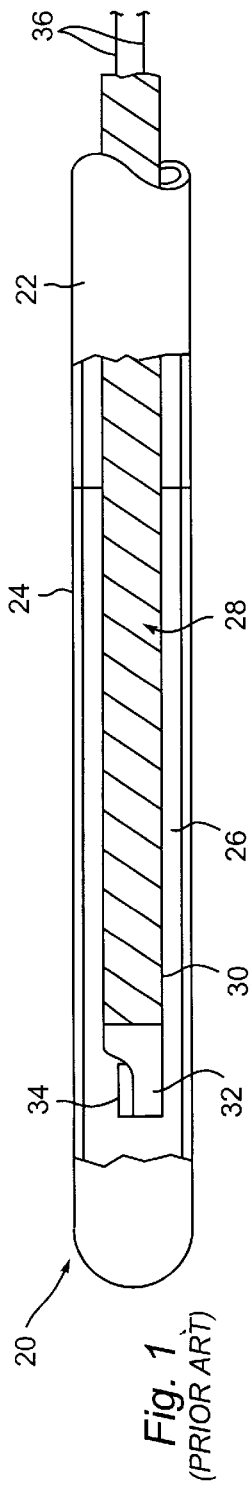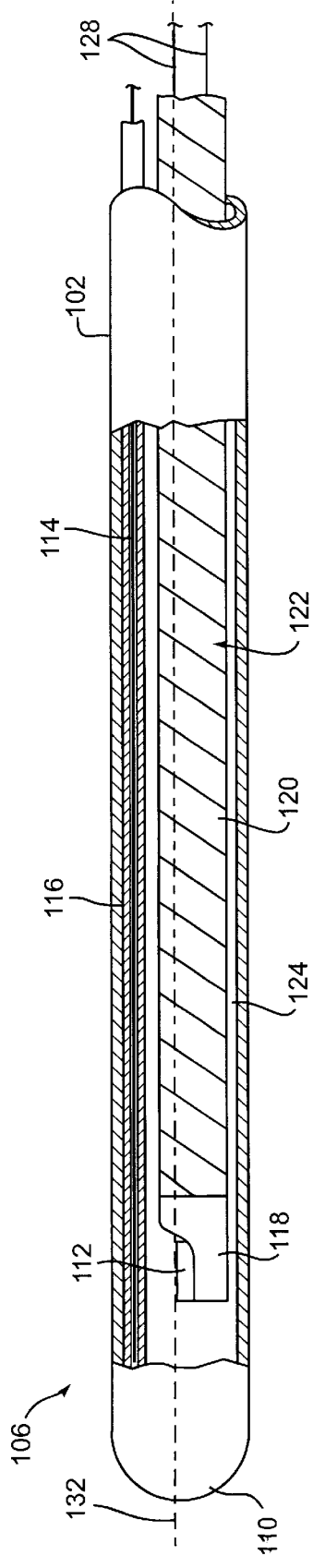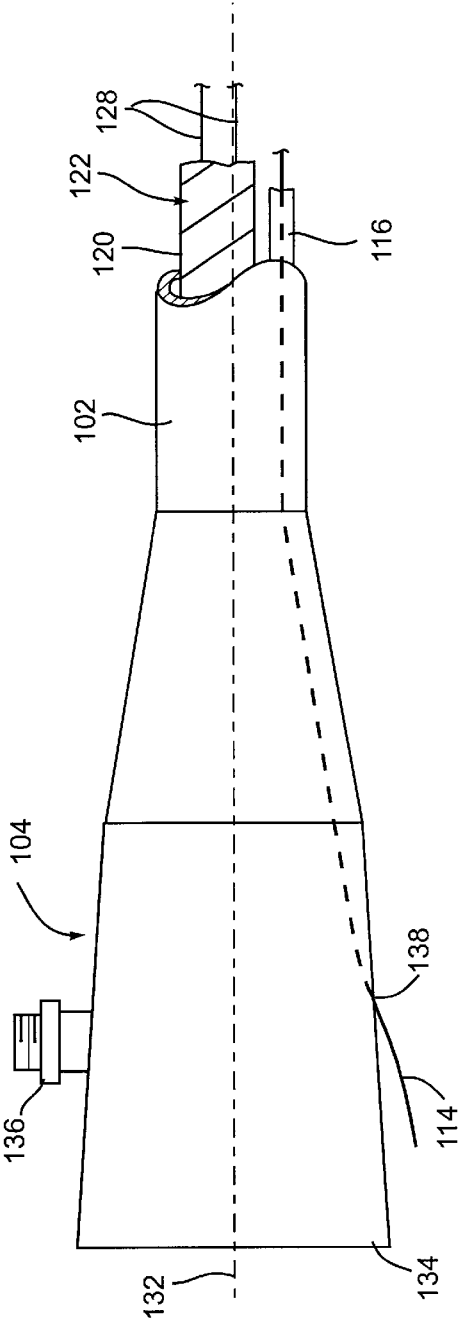

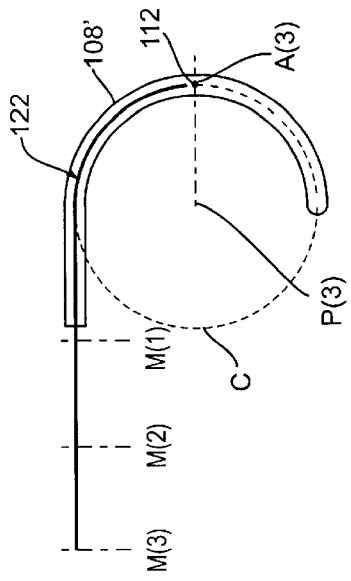
Fig. 7A
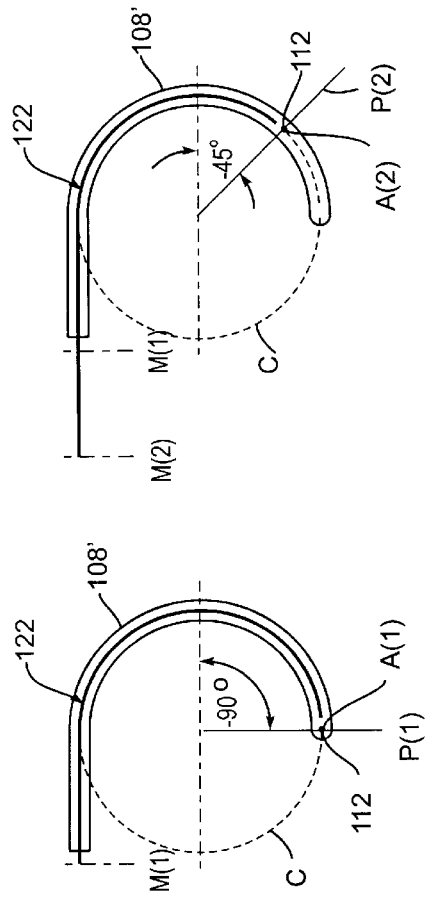
Fig. 7B
Fig. 7C
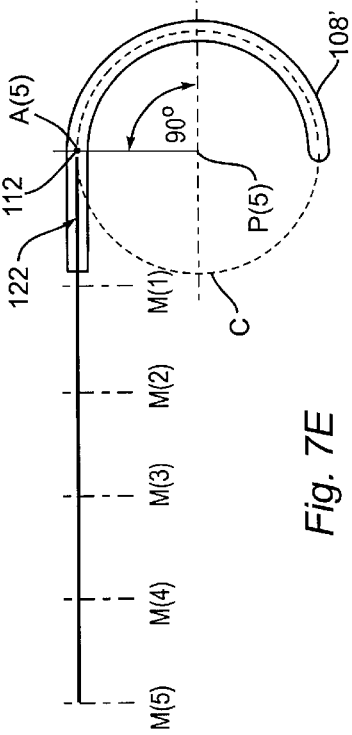
Fig. 7D
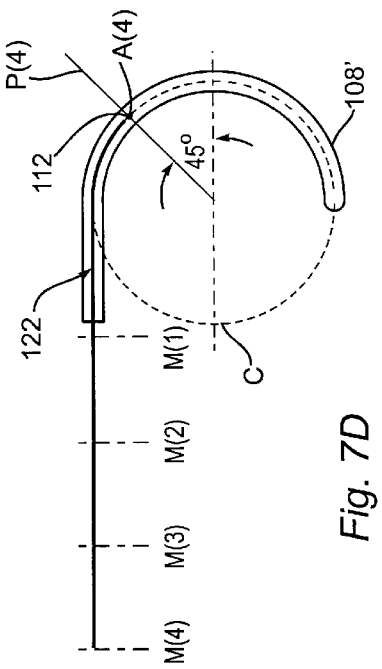
Fig. 7E

LOOP IMAGING CATHETER

FIELD OF THE INVENTION

The present invention pertains to medical imaging devices, and more particularly, to ultrasonic imaging catheters used in diagnostic applications.

BACKGROUND

Presently, minimally invasive imaging devices are employed in the diagnostic analysis of relatively large body cavities, such as, e.g., a heart chamber. Of particular interest to the present invention, ultrasonic imaging catheters have been employed to generate cross-sectional images from within the body cavity. The cross-sectional images reveal the surrounding contour of tissue, secondary structure, and other structural information relevant to treatment and diagnosis of various diseased conditions.

In this connection, a known imaging catheter 20, as depicted in FIG. 1, includes an elongate catheter body 22 with a distally formed elongate acoustic window 24 through which ultrasonic energy transparently passes. The catheter body 22 includes an imaging lumen 26 in which a rotatably and longitudinally translatable imaging core 28 is disposed. The imaging core 28 comprises a drive cable 30 along with a distally connected ultrasonic transducer housing 32 and mounted ultrasonic transducer 34. The transducer 34 is mechanically coupled to a drive unit (not shown) via the drive cable 30 and electrically coupled to a signal processor (not shown) via a transmission line 36 disposed in the drive cable 30. The transmission line 36 may consist of coaxial cable, triaxial cable, twisted pair, or other suitable configurations.

Disposal of the acoustic window 24, at a desired region within the body cavity and subsequent operation of the drive unit and signal processor, generates a longitudinal image scan of the tissue surrounding the body cavity. In particular, the electrical signals are transmitted to and received from the transducer 34, while the transducer 34 is rotationally and longitudinally translated relative to the acoustic window 24. In this manner, a multitude of imaging data "slices" are generated, which can be synthesized to produce a three-dimensional image of the body cavity for analysis by a viewing physician.

The ability to generate a three-dimensional image of a body cavity is advantageous in several respects. First, such an image generally allows a physician to ascertain the existence of a diseased region within the body cavity. Second, if such diseased region is found, the image permits a qualitative assessment of the nature of the disease in order to help select the most effective treatment modality. Third, the image can be used to determine the exact location of the diseased region, or the location of a therapeutic element relative to the diseased region, so that intervention can be directed only at the diseased region and not at healthy regions of the body cavity where the interventional procedure might cause damage.

Referring to FIG. 2, the imaging catheter 20 can be used to generate a three-dimensional image of a region of a heart 50. In particular, the imaging catheter 20 is advanced through the vasculature of the patient until the acoustic window 24 extends into a chamber of the heart 50, such as, e.g., the left ventricle 52. A longitudinal scan of the heart 50 is then performed, thereby generating a multitude of cross-sectional imaging data slices along respective imaging planes, such as, e.g., representative planes P(1)–P(5). Subsequent synthesis of the imaging data slices will result in a single three-dimensional image of heart tissue 50 which is intersected by the imaging planes. Heart tissue 50 not intersected by the imaging planes, such as, e.g., at the apex 54 of the heart 50, will not appear in the three-dimensional image. Thus, the image will not include potentially vital information that could lead to the proper diagnosis and subsequent treatment of a diseased region of the heart 50.

As shown in FIG. 3, the acoustic window 38 can be manipulated inside the heart 50, such that imaging planes of a subsequent longitudinal scan, such as, e.g., representative imaging planes P(6)–P(8), intersect heart tissue 50 not imaged during the first longitudinal scan, such as, e.g., at the apex 54. This task may sometimes be difficult or tedious to perform, and even if apparently successful, may result in a multitude of uncorrelated three-dimensional images, making proper examination of the heart 50 more difficult.

Further, referring back to FIG. 2, the force that the mitral valve 56 and entrance 58 to the left atrium 60 of the heart 50 exerts on the acoustic window 24 may create an arc 38 in the acoustic window 24 through which the heart 50 is imaged. As a result, the imaging data slices which are generated along the imaging planes, such as, e.g., planes P(4) and (P5), may, when synthesized, result in a image which is distorted at the left atrium 60 and right atrium 62, since the relative rotational orientation of the imaging planes P(4) and P(5) are unknown due to the randomness of the geometry of the arc 38.

SUMMARY OF THE INVENTION

The present invention overcomes the afore-described drawbacks of a conventional imaging device by providing an imaging device, such as, e.g., an ultrasonic imaging catheter, that includes a pull wire connected to the distal end thereof, such that manipulation of the pull wire forms the distal end of the imaging device into a curvilinear geometry that is known and repeatable.

In a first preferred embodiment, an ultrasonic imaging catheter, according to the present invention, includes an elongate catheter body with a distally formed acoustic window. An imaging core, which includes a drive cable and a distally mounted ultrasonic transducer, is disposed in an imaging lumen of the catheter body. The transducer is disposed in the acoustic window and is rotationally and longitudinally translatable relative thereto. The pull wire is disposed within a pull wire lumen, which may be the same as the imaging lumen, of the catheter body and is connected to the distal tip of the acoustic window. Longitudinal displacement of the pull wire, relative to the catheter body, causes the acoustic window to form into a known and repeatable arc. A stiffening member can be disposed along the acoustic window to provide resilience thereto.

In a preferred imaging method, the acoustic window of the catheter is placed within a cavity of an organ, such as, e.g., the left ventricle of a heart. The acoustic window is formed into an arc, and a curvilinear longitudinal imaging scan is performed through the arc, generating a multitude of cross-sectional imaging data slices respectively along a multitude of imaging planes. Due to the curvature of the acoustic window, the imaging planes have differing relative rotational orientations, which intersect the entire body cavity, thereby providing a single three-dimensional image of virtually the entire body cavity. Since the geometry of the arc is known, any distortion caused by the curvature of the acoustic window can be removed from the three-dimensional image.

In an alternatively preferred imaging method, the imaging catheter is used in conjunction with a therapeutic catheter having a distally located therapeutic element, such as, e.g., an ablation electrode. The acoustic window of the imaging catheter and the ablation electrode of the therapeutic catheter are placed in a body cavity, such as, e.g., the left ventricle of a heart. The imaging catheter is operated, in a similar manner as described above, to obtain a three-dimensional image of the left ventricle. The image generally will include an acoustic artifact caused by the ablation electrode, which can be used to locate the ablation electrode adjacent the diseased region of the left ventricle for subsequent ablation thereof.

In still another alternatively preferred imaging method, the imaging catheter is used in conjunction with another diagnostic catheter and a therapeutic catheter. The diagnostic catheter preferably includes a distal basket structure that includes an array of electrodes. The therapeutic catheter preferably includes a distal therapeutic element, such as, e.g., an ablation electrode. The acoustic window of the imaging catheter, the basket structure of the diagnostic catheter, and the ablation electrode of the therapeutic catheter are maneuvered into a body cavity, such as, e.g., the left ventricle of a heart. The diagnostic catheter is operated to locate the diseased region of the ventricle, with one of the diagnostic electrodes indicating the location thereof. The imaging catheter is operated in a similar manner, as described above, to obtain a three-dimensional image of body organ. The image may include a plurality of acoustic artifacts caused by the diagnostic electrodes and a single acoustic artifact caused by the ablation electrode, which can both be used to locate the ablation electrode adjacent the indicative diagnostic electrode, and thus, the diseased region, for subsequent ablation thereof.

Other and further objects, features, aspects, and advantages of the present invention will become better understood with the following detailed description of the accompanying drawings.

BRIEF DESCRIPTION OF THE DRAWINGS

The drawings illustrate both the design and utility of preferred embodiments of the present invention, in which:

FIG. 1 is a partially cut-away side view of a prior art ultrasonic imaging catheter configured for generating a longitudinal imaging scan of a body cavity;

FIG. 4A is a partially cut-away side view of the distal end of a preferred embodiment of an ultrasonic imaging catheter, wherein the acoustic window is configured to be formed into a known and repeatable curvilinear geometry;

FIG. 4B is a partially cut-away side view of the proximal end of the catheter of FIG. 4A;

FIGS. 7A–7E are partially cut-away side views of the curvilinear acoustic window of FIG. 6, particularly showing various imaging planes along which cross-sectional imaging data slices can be generated;

DETAILED DESCRIPTION OF THE PREFERRED EMBODIMENTS

Figure 2:
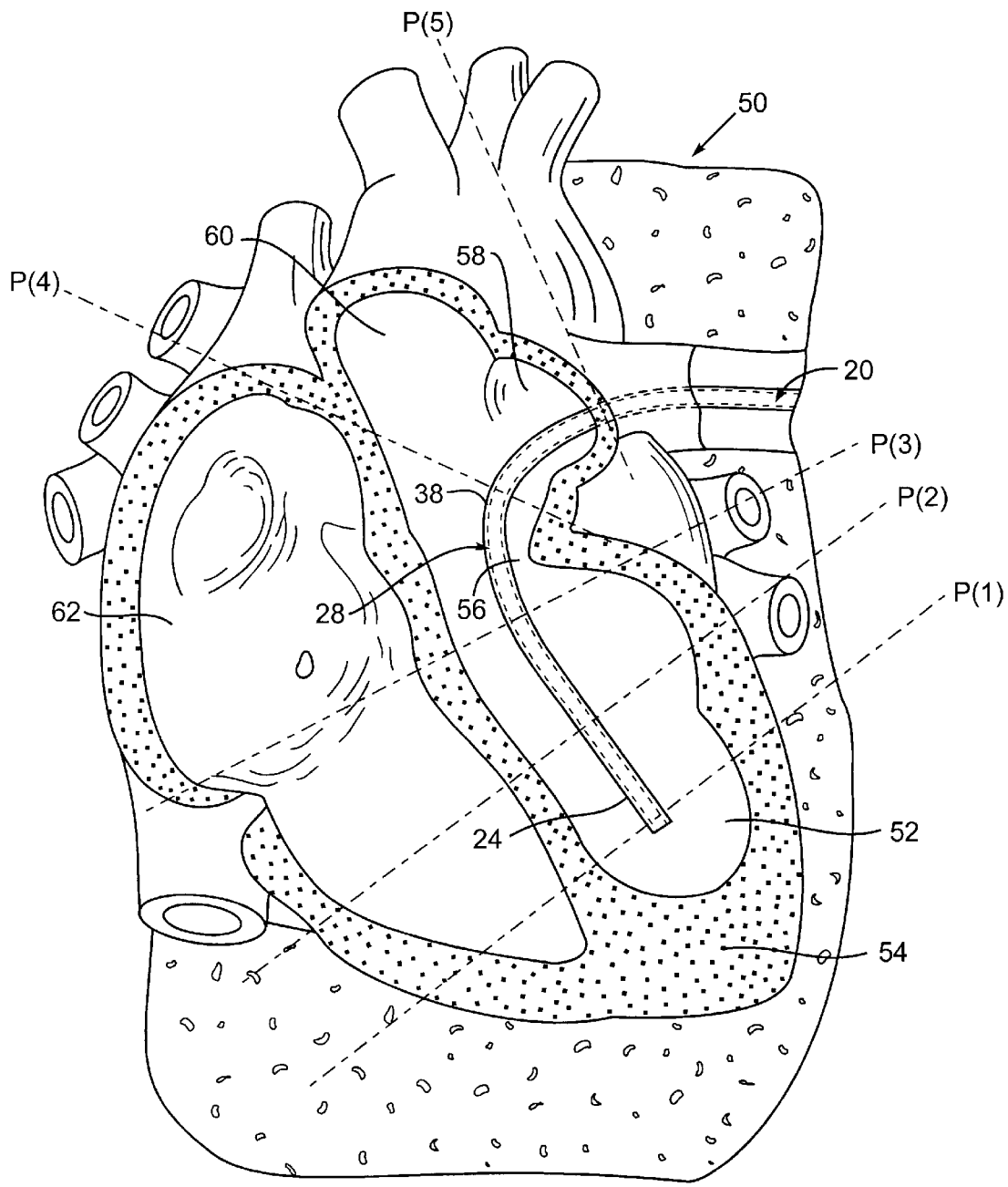
FIG. 2 is a plan view of the prior art catheter of FIG. 1 disposed within the left ventricle of a heart, particularly showing operation of the catheter to generate a multitude of cross-sectional imaging data slices of the heart.
Figure 3:
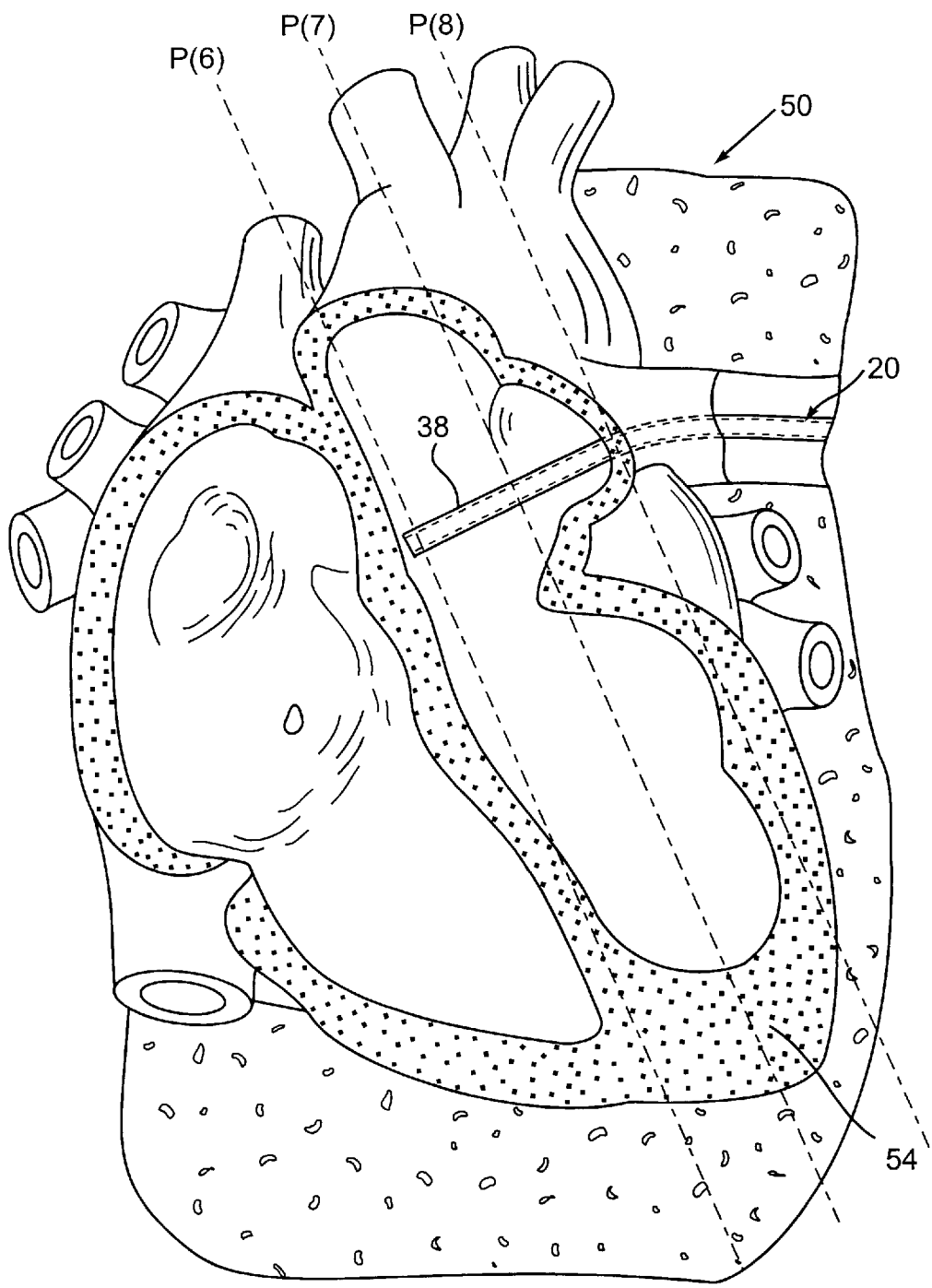
FIG. 3 is a plan view of the prior art catheter of FIG. 1 disposed within the left atrium of a heart, particularly showing operation of the catheter to generate a multitude of cross-sectional imaging data slices of the heart.

Referring to FIGS. 4A and 4B, a first exemplary loop imaging catheter 100, according to the present invention, is configured to provide a three-dimensional image of an organ with a relatively large cavity, such as, e.g., the heart 50 (FIGS. 2 and 3), when used in connection with a drive unit, signal processing circuitry and monitor (all not shown). The catheter 100 generally includes an elongate catheter body 102 with a proximal catheter end 104 (FIG. 4B) and a distal catheter end 106 (FIG. 4A), which forms a distal acoustic window 108 with a distal tip 110; a rotatably and longitudinally movable ultrasonic transducer 112 disposed in the acoustic window 108; a pull wire 114 connected to the distal tip 110 of the acoustic window 108; and a stiffening member 116 disposed in the acoustic window 108.

In particular, the catheter body 102 is composed of a biologically compatible material that provides both structural integrity to the imaging catheter 100, as well as a smooth outer surface for ease in axial movement through a patient's body passage (e.g., the vascular system) with minimal friction. Such materials are typically made from natural or synthetic polymers, such as, e.g., silicone, rubber, natural rubber, polyethylene, polyvinylchloride, polyurethanes, polyesters, polytetrafluoroethylenes (PTFE) and the like. The catheter body 102 may be formed as a composite having a reinforcement material incorporated within the polymeric body in order to enhance its strength, flexibility, and durability. Suitable enforcement layers include wire mesh layers, and the like. The flexible tubular elements of the catheter body 102 will normally be formed by extrusion. If desired, the catheter diameter can be modified by heat expansion and shrinkage using conventional techniques.

The acoustic window 108 is made of material that is substantially transparent to ultrasonic energy, such as, e.g., a low density polyethylene. The acoustic window 108 has an elongated length to facilitate longitudinal movement of the transducer 112 therein. It should be noted that the acoustic window 108 includes any structure that allows ultrasonic energy to be transmitted between the transducer 112 and body tissue.

The transducer 112 is mounted to a transducer housing 118, which is rotatably coupled to the drive unit via a flexible drive cable 120 to form an imaging core 122. The imaging core 122 is rotatably disposed within an imaging lumen 124, which extends substantially through the catheter body 102 from the acoustic window 108 to the proximal catheter end 104.

The drive cable 120 is preferably designed such that it possesses a high torsional stiffness and a low bending stiffness. For example, the drive cable 120 can be made of two counterwound layers of multifilar coils that are fabricated using techniques disclosed in Crowley et al., U.S. Pat. No. 4,951,677, which is fully incorporated herein by reference. The drive cable 120 is further reinforced to maintain its structural integrity during longitudinal movements thereof within the catheter body 102. The transducer 112 is electrically coupled to the signal processor via a transmission line 128, which are disposed in the drive cable 120.

Preferably, the drive unit is configured to automatically longitudinally translate the transducer 112, such as, e.g., the drive units described in Webler et al., U.S. Pat. No. 5,592,942, issued Jan. 14, 1997, and copending U.S. application Ser. No. 08/074,064, filed May 7, 1998, both of which are expressly and fully incorporated herein by reference. In this manner, longitudinal movement of the transducer 112 within the acoustic window 108 is controlled in a uniform and consistent manner.

The pull wire 114 and stiffening member 116 are both disposed in a pull wire lumen 130, which extends the length of the catheter body 102. The stiffening member 116 is composed of a suitable resilient material, such as, e.g., Nitinol, to provide resilience to the acoustic window 108. The stiffening member is preferably pre-shaped with a rectilinear geometry. The stiffening member 116 also acts as a conduit for the pull wire 114, allowing the pull wire 114 to be more easily longitudinally translated relative to the pull wire lumen 130. That is, the pull wire 114 is suitably attached to the distal tip 110 of the acoustic window 108 and extends through the center of the stiffening member 116 to the proximal catheter end 104. The pull wire 114 preferably comprises a non-corrosive material such as, e.g., stainless steel, which can be coated with a Teflon material to reduce the friction between the pull wire 114 and the stiffening member 116. As will be described in further detail below, the stiffening member 116 urges the acoustic window 108 into a rectilinear geometry, i.e., the longitudinal axis 132 of the acoustic window 108 is made rectilinear; while the pull wire 114 can be manipulated to configure the acoustic window 108 into a curvilinear geometry, i.e., the longitudinal axis 132 of the acoustic window 108 is made curvilinear. In alternative embodiments, the pull wire lumen 130 is the same as the imaging lumen 124.

The catheter 100 includes a catheter-drive unit interface 134, suitably mounted to the catheter body 102, to form the proximal catheter end 104 thereof. The catheter-drive unit interface 134 provides the mechanical interface through which the drive unit exerts longitudinal and torsional forces on the drive cable 120 to rotationally and longitudinally translate the transducer 112 relative to the acoustic window 108. The catheter-drive unit interface 134 also provides an electrical interface, typically via an inductive coupler (not shown), through which electrical signals are conveyed between the rotating transducer 112 and the stationary drive unit/signal processor. The drive unit-catheter interface 134 also includes an flush port 136, which is in fluid communication with the imaging lumen 124, to allow conveyance of ultrasonically transparent fluid therein. The drive unit-catheter interface 134 also includes a pull wire entry port 138 from which the pull wire 114 extends, allowing manipulation of the pull wire 114 to alternately form the acoustic window 108 into rectilinear and curvilinear geometries, as will be described in further detail below.

Figure 5:
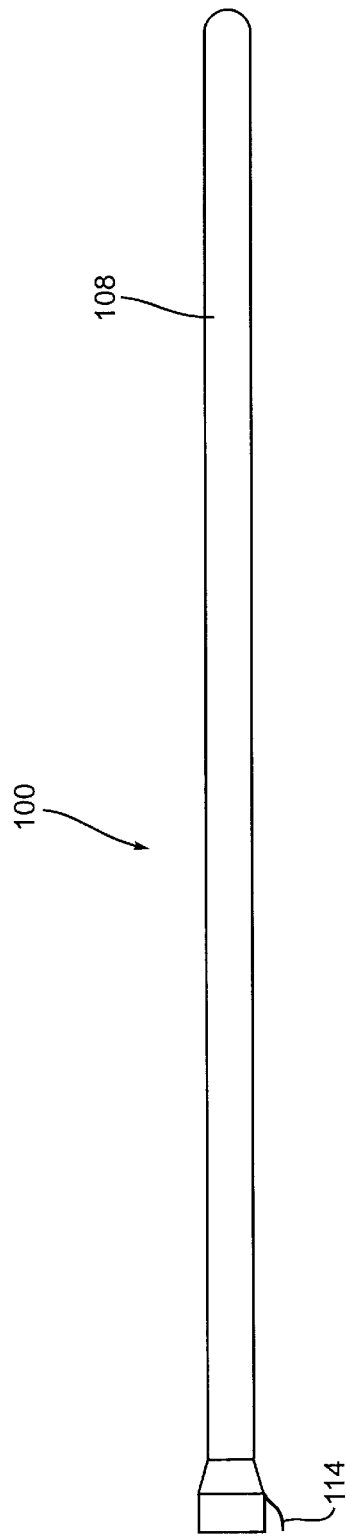
FIG. 5 is a side view of the catheter of FIGS. 4A and 4B, particularly showing the acoustic window in a rectilinear geometry.
Figure 6:
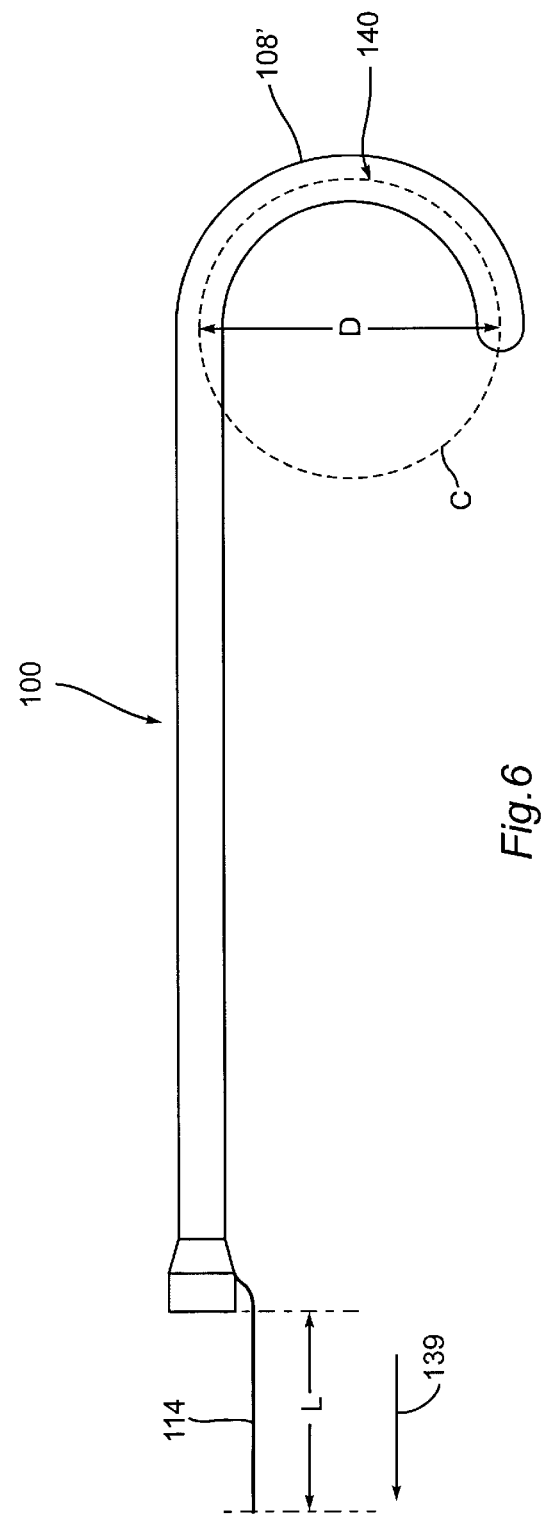
FIG. 6 is a side view of the catheter of FIGS. 4A and 4B, particularly showing the acoustic window in a curvilinear geometry.

As depicted in FIG. 5, when the pull wire 114 is in a relaxed state (i.e., the pull wire 114 is not tightened), the acoustic window 108 is placed into a substantially rectilinear geometry by the stiffening member 114. As depicted in FIG. 6, however, when the pull wire 114 is in a tensed state (i.e., the pull wire 114 is longitudinally displaced in a proximal direction relative to the acoustic window 108 as indicated by the arrow 139), the acoustic window 108 is subjected to a compressive force, bending the acoustic window 108 into a substantially circular arc 140 to form a curvilinear acoustic window 108'. The geometry of the circular arc 140 is known and repeatable in that longitudinal displacement of the pull wire 114 by a certain distance L consistently results in a circular arc 140 with a certain circumference C.

The circular arc 140 allows the catheter 100 to image body tissue along various imaging planes. Referring to FIGS. 7A–7E, operation of the drive unit with the pull wire 114 longitudinally displaced a distance L, allows cross-sectional images to be generated along representative imaging planes P(1)–P(5) when the transducer 112 is respectively located at corresponding points A(1)–A(5) along the circumference C of the curvilinear acoustic window 108'. As will be described in further detail below, such a capability facilitates the generation of a three-dimensional image of substantially the entire body cavity via a single longitudinal imaging scan.

The origin and relative rotational orientation of each imaging plane can be determined from the corresponding longitudinal displacement M of the transducer 112. For instance, if the transducer 112 is displaced a distance M(3), as depicted in FIG. 7C, it is known that the imaging plane P(3) has an origin at point A(3) along the circumference C of the curvilinear acoustic window 108' and has a relative rotational position of 0°. Similarly, if the transducer 112 is displaced a distance M(5), as depicted in FIG. 7E, it is known that the imaging plane P(5) has an origin at point A(5) along the circumference C of the curvilinear acoustic window 108' and has a relative rotational position of 90°. As will be described in further detail below, such a capability facilitates the generation of a three-dimensional image of a body cavity that is not distorted.

Figure 8:
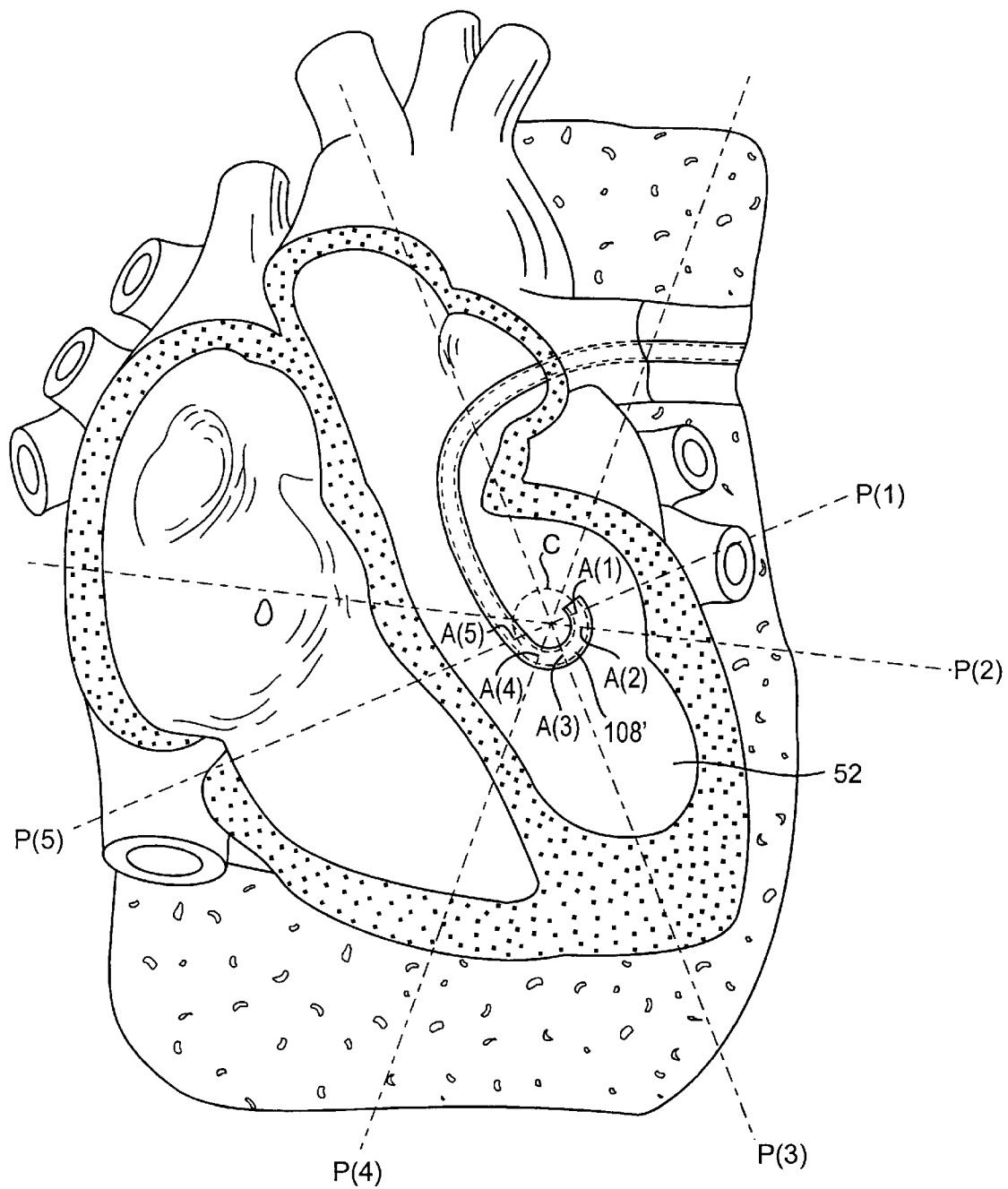
FIG. 8 is a plan view of the catheter of FIGS. 4A and 4B disposed within the left ventricle of a heart, particularly showing operation of the catheter to generate a multitude of cross-sectional imaging data slices of the heart through the curvilinear acoustic window.

With reference to FIG. 8, operation of the catheter 100 can now be described in connection with the diagnosis of a body organ with a relatively large cavity, such as, e.g., the heart 50. The catheter body 102 is introduced into a patient's body through an entrance point, such as, e.g., the femoral artery, and routed through the vasculature via a guide wire and/or guide sheath (not shown) until the acoustic window 108 is disposed within the left ventricle 52 of the heart 50. Ultrasonically transparent fluid, such as, e.g., saline solution, is conveyed into the imaging lumen 124 via the flush port 136 to fill the acoustic window 108 (FIGS. 4A and 4B), enabling the transmission and reception of ultrasonic energy through the fluid, through the acoustic window 108 and to and from the human anatomy. The pull wire 114 is then manipulated to form the curvilinear acoustic window 108', i.e., the pull wire 114 is longitudinally displaced the distance L, such that the curvilinear acoustic window 108' forms the arc 140 with the known circumference C (FIG. 6).

The imaging core 122 is positioned within the catheter body 102, such that the transducer 112 is located at the most distal point A(1) on the circumference C of the curvilinear acoustic window 108' (FIG. 7A). The drive unit is then operated to rotationally and longitudinally translate the transducer 112 from point A(1) to point A(5) along the circumference (C) of the curvilinear acoustic window 108' (FIGS. 7A–7E), while transmitting and receiving electrical signals to the transducer 112. In this manner, a curvilinear longitudinal imaging scan of the heart 50 is performed. That is, a multitude of raw cross-sectional imaging data slices are generated respectively along a multitude of continuously varying imaging planes, which perpendicularly intersect the circumference C of the curvilinear acoustic window 108'. For purposes of brevity in illustration, FIG. 8 depicts only the five representative imaging planes P(1)–P(5) at respective points A(1)–A(5) along the circumference (C) of the curvilinear acoustic window 108'. In this manner, the imaging planes intersect virtually the entire heart tissue 50, and thus, the multitude of raw imaging data slices include all of the information necessary to perform a comprehensive analysis of the heart 50.

If synthesized, these raw imaging data slices would result in a multitude of cross-sectional images, which without alteration would result in a three-dimensional image of the heart 50 that is distorted due to the curvature of the curvilinear acoustic window 108'. The signal processor, however, removes any distortion in the three-dimensional image that would result from the raw cross-sectional images based on the known curvature of the curvilinear acoustic window 108'. That is, a multitude of processed cross-sectional imaging data slices are generated, each of which is based on a corresponding raw imaging data slice, the known circumference C of the arc 140, and a corresponding longitudinal displacement M of the transducer 112. For example, the raw imaging data slice along the imaging plane P(2) can be modified based on the circumference C of the arc 140 and the longitudinal displacement M(2) of the transducer 112, resulting in a corresponding processed imaging data slice. As described with respect to FIGS. 7A–7E, the circumference C of the arc 140 can be determined from the longitudinal displacement L of the pull wire 114; and the origin and rotational orientation of each of the imaging planes P can be determined from the corresponding longitudinal displacements M of the transducer 112.

Alternatively, the circumference C of the curvilinear acoustic window 108' can be determined based on the particular imaging plane that is coextensive with the diameter D of the curvilinear acoustic window 108' (FIG. 6), and in this case imaging planes P(1) or P(5). In particular, if an imaging data slice is generated along one of these imaging planes, it will include an acoustic artifact caused by the pull wire 114, thereby allowing determination of the diameter D, and thus the circumference C of the curvilinear acoustic window 108'. For instance, if the imaging data slice is generated along imaging plane P(1), the imaging data slice will include an acoustic artifact at point P(5), thereby allowing the distance between P(1) and P(5), i.e., the diameter D, to be calculated.

The multitude of processed imaging data slices are then synthesized, generating a single undistorted three-dimensional image of substantially the entire heart 50, which appears on the monitor for analysis by a viewing physician. The heart 50 can then be properly analyzed to determine the existence and extent of any diseased tissue within the heart 50. The pull wire 114 can then be relaxed, so that the stiffening member 116 urges the curvilinear acoustic window 108 back into its rectilinear geometry, allowing the catheter 100 to be extracted from the vasculature of the patient.

The adverse effects that cardiac motion may have on the accuracy of the three-dimensional image may be minimized by gating the acquisition of the raw imaging data slices to coincide with the resting period (period of minimal movement of heart tissue) of the cardiac cycle.

Figure 9:
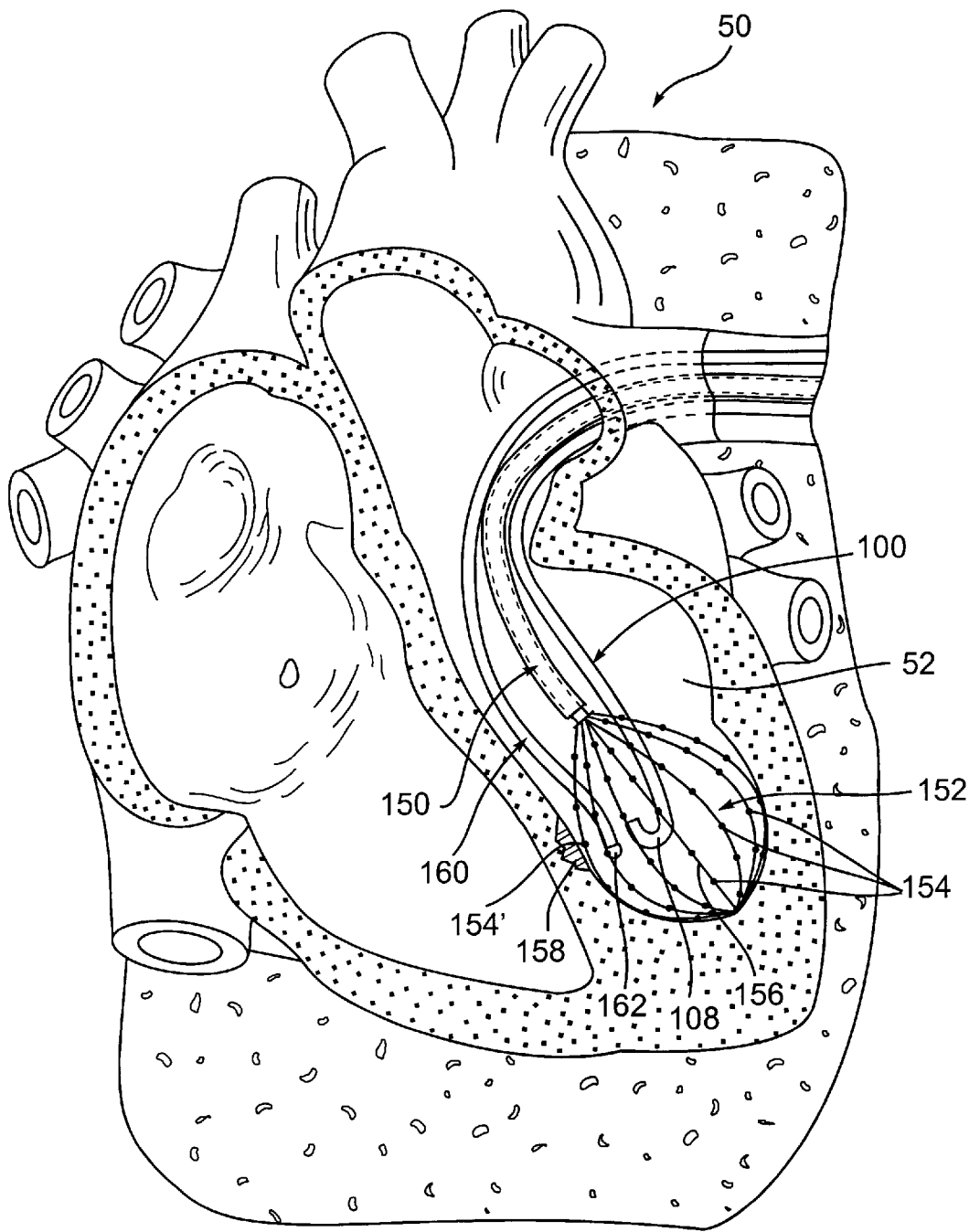
FIG. 9 is a plan view of the catheter of FIGS. 4A and 4B, a diagnostic catheter and a therapeutic catheter disposed within the left ventricle of a heart, wherein the diagnostic catheter is operated to locate a diseased region, and the imaging catheter is operated to locate an ablation electrode of the therapeutic catheter adjacent the diseased region.

The loop imaging catheter 100 can be employed with other diagnostic and/or therapeutic equipment to more effectively diagnose and treat diseased regions within a body cavity. For instance, as depicted in FIG. 9, the catheter 100 can be employed with a diagnostic catheter 150 and an ablation catheter 160 to diagnose and treat infarcted tissue 158 within the left ventricle 52 of the heart 50.

The diagnostic catheter 150 is configured to locate infarcted tissue 158 (i.e., an area of dead tissue caused by insufficient blood supply) within the heart 50 and includes a distally located basket structure 152, which carries an array of electrodes 154 on a multitude of resilient splines 156. Localization of the infarcted tissue 158 is accomplished by transmitting electrical signals between selected pairs of electrodes 154 (bipolar mode) or between selected electrodes 154 and an indifferent electrode (unipolar mode), and subsequently analyzing the received electrical signals. The ablation catheter 160 includes an ablation electrode 162, which is configured to thermally destroy myocardial tissue, either by heating or cooling the tissue. Further details concerning the structure and method of using the diagnostic catheter 150 and ablation catheter 160 are disclosed in Panescu et al., U.S. Pat. No. 5,577,509, issued Nov. 26, 1996, which is fully and expressly incorporated herein by reference.

In operation, the basket structure 152 of the diagnostic catheter 150, the ablation electrode 162 of the ablation catheter 160, and the acoustic window 108 of the imaging catheter 100 are configured within the left ventricle 52. The diagnostic basket structure 152 is configured into firm contact with the myocardial tissue of the left ventricle 52 and operated to locate any infarcted tissue 158 within the left ventricle 52. The location of the infarcted tissue 158 can be expressed in terms of a specific electrode 154' within the array of electrodes 154.

Once the infarcted tissue 158 is located, the acoustic window 108 of the imaging catheter 100 is formed into the curvilinear acoustic window 108', and a curvilinear longitudinal imaging scan is performed to generate a three-dimensional image of the left ventricle 52, in a similar manner as that described above with respect to FIG. 8. Within the image, there will appear an array of acoustic artifacts caused by the array of diagnostic electrodes 154 and a single acoustic artifact caused by the ablation electrode 162. One of the array of acoustic artifacts represents the indicative electrode 154', thereby providing knowledge of the location of the ablation electrode 162 relative to the indicative electrode 154'. The ablation electrode 162 can then be precisely placed into firm contact with the infarcted tissue 158 for subsequent ablation thereof. Prior to ablation, the imaging catheter 100 can again be operated to ensure that the ablation electrode 162 is in fact in firm contact with the infarcted tissue 158.

The loop imaging catheter 100 can be employed with therapeutic equipment, with the imaging catheter 100 being used as the sole diagnostic device. For instance, the loop imaging catheter 100 and ablation catheter 160 can be disposed in the cavity of a body organ, such as, e.g., the ventricle 52 of the heart 50. The imaging catheter 100 can be operated to perform a curvilinear longitudinal imaging scan, generating a three-dimensional image of the left ventricle 52. In the image there may appear a diseased region 158 and an acoustic artifact caused by the ablation electrode 162. With knowledge of the location of the ablation electrode 162 relative to the location of the diseased region 158 obtained from the acoustic artifact, the ablation electrode 162 can be precisely placed into firm contact with the diseased region 158 for subsequent ablation thereof.

While preferred embodiments have been shown and described, it will be apparent to one of ordinary skill in the art that numerous alterations may be made without departing from the spirit or scope of the invention. Therefore, the invention is not to be limited except in accordance with the following claims.

What is claimed:

1. An imaging device, comprising:
   an elongate tubular body including a distal elongate acoustic window, the tubular body forming an imaging lumen and a pull wire lumen;
   an imaging core disposed in the imaging lumen, the imaging core including a drive cable and a distally disposed ultrasonic transducer, the transducer being disposed in the acoustic window and rotatably and longitudinally movable relative to the acoustic window; and
   a pull wire disposed in the pull wire lumen, the pull wire being mechanically coupled to the acoustic window.

2. The imaging device of claim 1, wherein the imaging lumen and pull wire lumen are distinct.

3. The imaging device of claim 1, wherein the elongate tubular body is a catheter body.

4. The imaging device of claim 1, further comprising a stiffening member disposed along the acoustic window.

5. The imaging device of claim 4, wherein the stiffening member is configured to urge the acoustic window into a rectilinear geometry, and wherein the pull wire is configured to allow manipulation of the acoustic window into a curvilinear geometry.

6. The imaging device of claim 5, wherein the acoustic window is configured to form a known substantially circular arc when the pull wire is displaced a certain longitudinal distance.

7. The imaging device of claim 4, wherein the stiffening member is a tube disposed in the pull wire lumen, and wherein the pull wire is disposed in the stiffening member.

8. The imaging device of claim 1, wherein the pull wire is connected to a distal tip of the acoustic window.

9. A method of imaging a body cavity using an imaging device, the imaging device including a distal end and configured for performing a longitudinal scan of the body cavity, the method comprising:
   advancing the distal end of the imaging device into the body cavity;
   bending the distal end of the imaging device into a predetermined arc; and
   performing a longitudinal scan of the body cavity through the arc to generate a plurality of imaging data slices respectively along a plurality of imaging planes, the plurality of imaging planes having differing relative rotational orientations.

10. The method of claim 9, wherein the imaging device further includes a pull wire mechanically coupled to a distal tip of the imaging device, and wherein the pull wire is longitudinally displaced to bend the distal end of the imaging device into the arc.

11. The method of claim 9, further comprising determining the circumference of the arc.

12. The method of claim 11, wherein the circumference of the arc is selectively determinable based on the longitudinal displacement of the pull wire.

13. The method of claim 11, wherein the longitudinal scan is performed through the pull wire to generate an acoustic artifact in at least one of the imaging data slices, and the circumference of the arc is determined based on the acoustic artifact.

14. The method of claim 11, wherein the plurality of imaging data slices are distorted, and wherein the method further comprises generating a plurality of processed imaging data slices, each of which is derived from a corresponding imaging data slice, the circumference of the arc, and a corresponding longitudinal displacement of the ultrasonic transducer.

15. The method of claim 14, further comprising generating a three-dimensional image of the body cavity based on the plurality of processed imaging data slices.

16. The method of claim 9, wherein the body cavity is a heart chamber.

17. The method of claim 9, wherein the imaging device is an ultrasonic imaging catheter.

18. A method of imaging a body cavity using an imaging catheter and a therapeutic catheter, the imaging catheter including a distal end and configured for performing a longitudinal scan of the body cavity, the therapeutic catheter including a therapeutic element and configured for treating diseased tissue, the method comprising:
   advancing the distal end of the imaging catheter into the body cavity;
   advancing the therapeutic element of the therapeutic catheter into the body cavity;
   bending the distal end of the imaging device into a predetermined arc with a known circumference;
   performing a curvilinear longitudinal scan of the body cavity through the arc to generate a plurality of imaging data slices respectively along a plurality of imaging planes with differing relative rotational orientations;
   generating a three-dimensional image of the body cavity based on the plurality of imaging data slices, and determining the location of a diseased region in the body cavity based on the image; and
   treating the diseased region with the ablation electrode.

19. The method of claim 18,
   wherein at least one of the plurality of imaging data slices includes an acoustic artifact caused by the therapeutic element; and
   further comprising locating the therapeutic element adjacent the diseased region based on the acoustic artifact.

20. The method of claim 18, further using a diagnostic catheter with a distal basket structure, the diagnostic catheter configured for locating diseased tissue, the method further comprising:
   advancing the basket structure of the diagnostic catheter into the body cavity; and
   diagnosing the body cavity with the diagnostic catheter to locate the diseased tissue.

21. The method of claim 20,
   wherein the basket structure includes an array of diagnostic electrodes;
   wherein at least one of the imaging data slices includes an acoustic artifact caused by a diagnostic electrode that is indicative of the diseased tissue location, and at least one of the imaging data slices includes an acoustic artifact caused by the therapeutic element; and
   further comprising locating the therapeutic element adjacent the diseased region based on the acoustic artifacts.

* * * * *